United States Patent
Yoshioka et al.

(10) Patent No.: US 7,582,076 B2
(45) Date of Patent: Sep. 1, 2009

(54) OPEN-TYPE DISPOSABLE WEARING ARTICLE

(75) Inventors: Toshiyasu Yoshioka, Kagawa-ken (JP); Yasushi Sayama, Kagawa-ken (JP)

(73) Assignee: Uni-Charm Corporation, Ehime-Ken (JP)

(*) Notice: Subject to any disclaimer, the term of this patent is extended or adjusted under 35 U.S.C. 154(b) by 1125 days.

(21) Appl. No.: 10/227,842

(22) Filed: Aug. 27, 2002

(65) Prior Publication Data

US 2003/0045854 A1 Mar. 6, 2003

(30) Foreign Application Priority Data

Aug. 31, 2001 (JP) .............................. 2001-263368

(51) Int. Cl.
*A61F 13/15* (2006.01)

(52) U.S. Cl. ...................................... 604/387; 604/391

(58) Field of Classification Search .......... 604/386–391
See application file for complete search history.

(56) References Cited

U.S. PATENT DOCUMENTS 4,670,012 A * 6/1987 Johnson ........................ 604/390
5,653,704 A * 8/1997 Buell et al. .............. 604/385.3
5,851,205 A * 12/1998 Hisada et al. ................ 604/390
5,968,030 A * 10/1999 Shimizu et al. ............. 604/390
6,254,583 B1 * 7/2001 Coates ................... 604/385.14

FOREIGN PATENT DOCUMENTS

| EP | 0 211 197 | 2/1987 |
|---|---|---|
| EP | 0 756 855 | 2/1997 |
| EP | 0 941 728 | 9/1999 |
| EP | 1 062 931 | 12/2000 |
| JP | 1997-75393 A | 3/1997 |
| WO | WO 96 32084 | 10/1996 |
| WO | WO 00 74621 | 12/2000 |

* cited by examiner

*Primary Examiner*—Michele Kidwell
(74) *Attorney, Agent, or Firm*—Lowe Hauptman Ham & Berner

(57) ABSTRACT

Here is disclosed an open-type disposable wearing article composed of a front waist region, a rear waist region and a crotch region extending between these waist regions wherein tape fasteners used to connect the front and rear waist to each other are attached to side flaps in the rear waist region and each of the side flaps has a first zone adapted to cover a surface facing a wearer's body of the fixed end portion of the associated tape fastener and a second zone defined by the side flap except for the first zone and wherein the first zone has a basis weight higher than that of the second zone.

10 Claims, 5 Drawing Sheets

OPEN-TYPE DISPOSABLE WEARING ARTICLE

BACKGROUND OF THE INVENTION

This invention relates to an open-type disposable wearing article.

Japanese Patent Publication No. 1997-75393 A discloses a disposable diaper comprising a liquid-pervious topsheet, a liquid-impervious backsheet and a liquid-absorbent core interposed between these two sheets so as to configure, in a longitudinal direction, front and rear waist regions and a crotch region extending between these waist regions wherein a pair of side flaps extending in the longitudinal direction along both sides of the rear waist region are provided with tape fasteners used to connect the front and rear waist regions.

Each of the tape fasteners has a fixed end portion bonded to the associated side flap and a free end portion extending outward from the fixed end portion in a transverse direction. The fixed end portion is shaped substantially in a rectangle which is relatively long in the longitudinal direction, and has first and second outer corners put aside toward the side edge of the side flap and first and second inner corners put aside toward the middle of the diaper. The fixed end portion is interposed between the topsheet and a plastic sheet extending outward in the transverse direction from the associated side portion of the backsheet and bonded to respective inner surfaces of the topsheet and the plastic sheet. The free end portion is coated on its surface facing a wearer's body with a self-adhesive. In each of the tape fasteners, the free end portion is folded back toward the inside of the diaper and temporarily fastened to the outer surface of the topsheet by means of a self-adhesive in such a manner to be released.

In the front waist region, the backsheet is provided on its outer surface with target tape strips bonded thereto. These target tape strips serve as landing zones for the respective free end portions of the tape fasteners. The tape fasteners are made of flexible plastic sheets having stiffness higher than those of the top- and backsheets so that the front and rear waist regions of the diaper may be reliably connected to each other. The target tape strips are made of a plastic film.

To wear the diaper, the side flaps in the rear waist region may be placed upon outer sides of the respective side flaps in the front waist region, then the free end portions of the respective tape fasteners may be anchored on the target tape strips by means of a self-adhesive and thereby the front and rear waist regions may be connected to each other. With the front and rear waist regions connected together in this manner, the diaper defines a waist-hole and a pair of leg-holes lying below the waist-hole.

With the diaper disclosed in the above-cited Publication, movement of the person wearing this diaper may causes the side flaps in the front waist region to be curled up and the side flaps in the rear waist region to contact the diaper wearer's body. Also depending on the basis weight of the topsheet, the inner and outer corners of the tape fasteners' fixed end portions may sometimes be exposed on the outer surface of the topsheet as the side flaps in the rear waist region come in contact with the wearer's body. In consequence, the fixed end portions may bite into the wearer's body and give the wearer pain and/or uncomfortable feeling.

SUMMARY OF THE INVENTION

It is an object of this invention to provide a disposable wearing article improved so that there is no anxiety that fixed end portions of tape fasteners might give a wearer pain and/or uncomfortable feeling even when the side flaps in the rear waist region come in contact with the wearer's body.

According to this invention, there is provided an open-type disposable wearing article which is including side flaps extending in a longitudinal direction and end flaps extending in a transverse direction and composed of, in the longitudinal direction, front and rear waist regions and a crotch region extending between these waist regions, wherein the flexible tape fasteners used to connect the front and rear waist regions are attached to the side flaps extending in the rear waist region, and each of the tape fasteners have a fixed end portion secured to the associated one of the side flap and a free end portion extending outward from the fixed end portion in the transverse direction, and anchoring means adapted to be anchored on the front waist region are formed on the surface of the free end portions facing a wear's body.

This invention is further comprises the side flaps which have first zones covering the respective surface of the fixed end portions facing a wearer's body in the respective tape fasteners and second zones, where a basis weight of the first zones is higher than that of the second zones.

According to one preferred embodiment of this invention, the first zones have a basis weight in a range of 15-100 $g/m^2$ and the second zones have a basis weight in a range of 10-30 $g/m^2$ and the tape fasteners have flexural stiffness in a range of 0.3-10 $g \cdot cm^2/cm$.

According to another preferred embodiment of this invention, the fixed end portions of the tape fasteners respectively have a substantially rectangular shape in plan view thereof and respectively include first and second outer corners put aside toward transversely opposite side edges of the side flaps and first and second inner corners put aside toward the middle of the article, of which at least the first and second outer corners are covered with the first zones of the side flaps.

According to still another preferred embodiment of this invention, the side flaps are formed by a sheet material more flexible than the tape fasteners and the first zones of the side flaps are formed by two or more of the sheets placed upon each other.

DETAILED DESCRIPTION OF THE PREFERRED EMBODIMENTS

Details of an open-type disposable wearing article according to this invention will be more fully understood from the description of the disposable diaper for absorption and containment of bodily discharges given hereunder in reference to the accompanying drawings.

Figure 1:
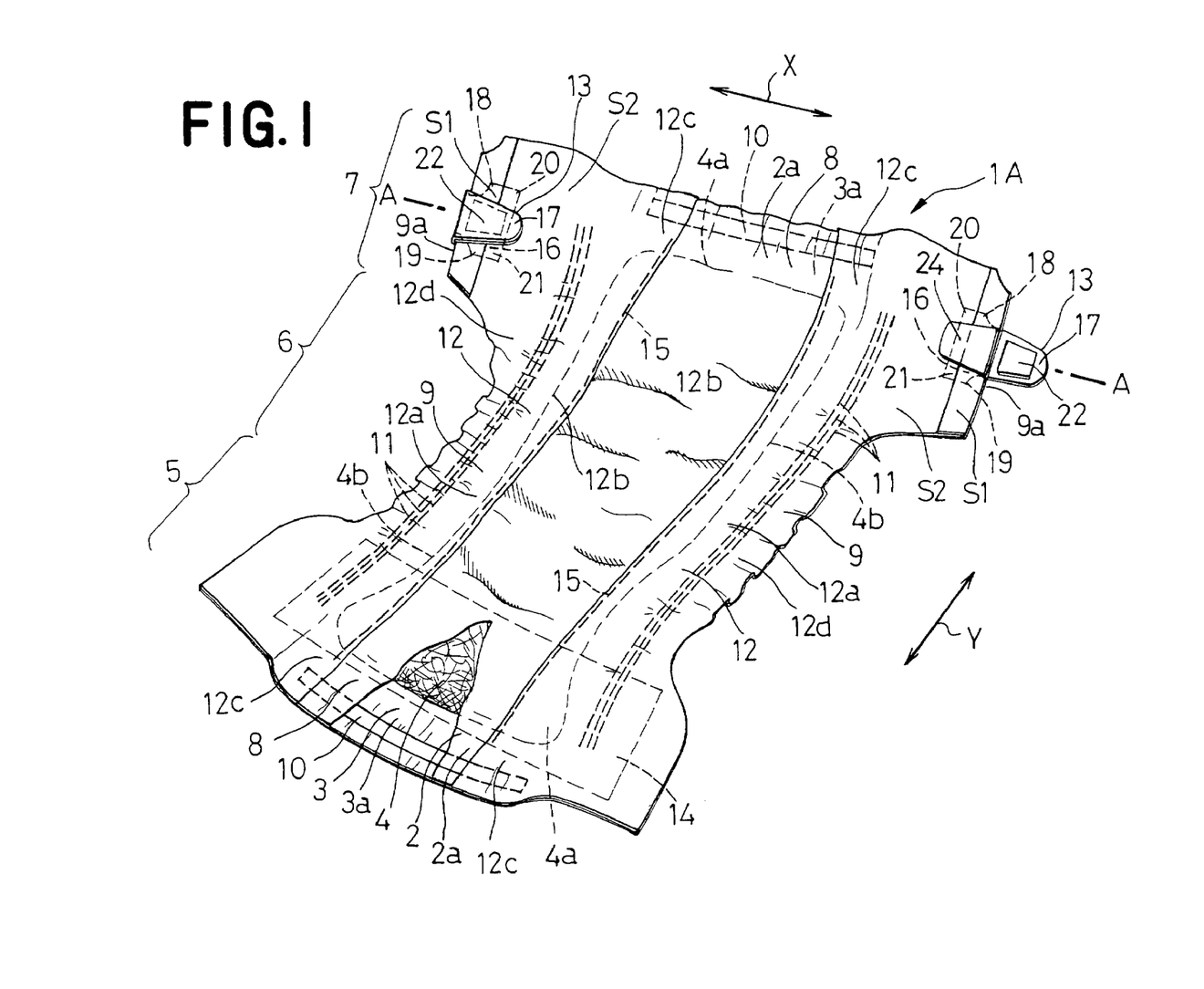
FIG. 1 is a partially cutaway perspective view of the disposable diaper in which a middle portion is shown in a simplified manner.
Figure 2:
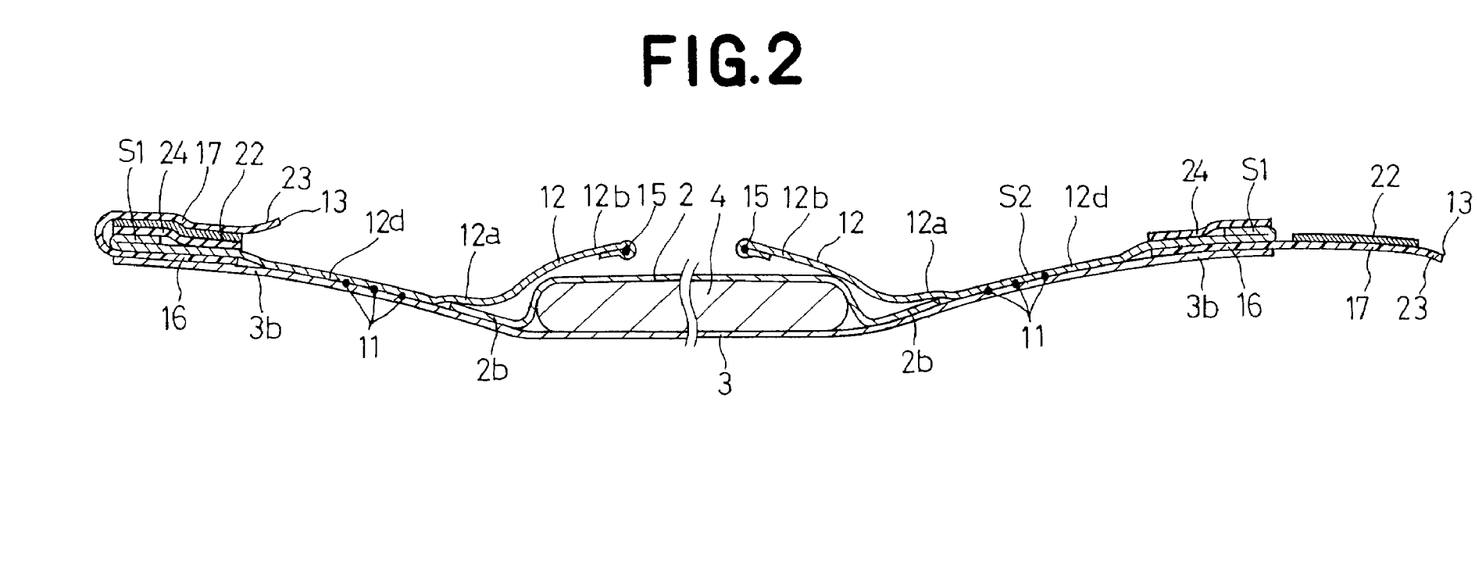
FIG. 2 is a sectional view taken along a line A-A in FIG. 1.

FIG. 1 is a partially cutaway perspective view of the disposable diaper 1A in which a middle portion is shown in a simplified manner and FIG. 2 is a sectional view taken along a line A-A in FIG. 1. FIG. 1 shows one of tape fasteners 13 as its free end portion 17 has been unfolded outward in a transverse direction of the diaper 1A. In FIG. 1, the transverse direction is indicated by an arrow X and a longitudinal direction is indicated by an arrow Y. "Inner surfaces" of top- and backsheets 2, 3 and leak-proof sheets 12 should be understood to mean the respective surfaces of these sheets 2, 3, 12 facing a core 4 and "outer surfaces" of these sheets 2, 3, 12 facing away from the core 4. "Surfaces facing a wearer's body" of fixed end portions 16 and the free end portions 17 of the tape fasteners 13 should be understood to mean the surfaces of these portions 16, 17 facing a body of person wearing the diaper 1A.

The diaper 1A basically comprises the liquid-pervious topsheet 2 facing the wearer's body, the liquid-impervious backsheet 3 facing away from the wearer's body and the liquid-absorbent core 4 interposed between these two sheets 2, 3. The core 4 is bonded to the inner surface of at least one of the top- and backsheets 2, 3.

The diaper 1A is composed of, in a longitudinal direction, a front waist region 5, a rear waist region 7 and a crotch region 6 extending between these waist regions 5, 7. In the front and rear waist regions, a pair of end flaps 8 extend in the transverse direction and a pair of side flaps 9 extend in the longitudinal direction. In the crotch region 6, the side flaps 9 describe circular arcs which are convex inward in the transverse direction of the diaper 1A.

The end flaps 8 are respectively provided with band-like waist-surrounding elastic members 10 which are extending in the transverse direction and attached thereto in a stretched state. In the crotch region 6, the side flaps 9 are respectively provided with a plurality of thigh-surrounding elastic members 11 which are extending in the longitudinal direction and attached thereto in a stretched state. Substantially liquid-impervious leak-proof sheets 12 extending in the longitudinal direction are attached to the respective side flaps 9. In the rear waist region 7, a pair of tape fasteners 13 are attached to the side flaps 9. In the front waist region 5, a rectangular target tape strip 14 is attached on an outer surface of the backsheet 3 serving as a landing zone for the tape fasteners 13.

Each of the leak-proof sheets 12 has a fixed side edge portion 12a extending in the longitudinal direction immediately outside the associated side edge 4b of the core 4, a free side edge portion 12b extending in the longitudinal direction and normally tends to rise on the topsheet 2 and longitudinally opposite end portions 12c collapsed inward in the transverse direction of the diaper 1A. Each of the leak-proof sheets 12 further has a lateral portion 12d extending outward from the fixed side edge portion 12a in the transverse direction. The free side edge portion 12b is provided with a stretchable elastic member 15 extending in the longitudinal direction and attached thereto in a stretched state. The elastic member 15 is covered with a part of the free side edge portion 12b.

In the end flaps 8, longitudinally opposite end portions 2a of the topsheet 2 and longitudinally opposite end portions 3a of the backsheet 3 extending outward beyond longitudinally opposite ends 4a of the core 4 are overlaid and respective inner surfaces of the sheets 2, 3 are joined together along these end portions 2a, 3a. The waist-surrounding elastic members 10 are respectively interposed between the end portions 2a of the topsheet 2 and the end portions 3a of the backsheet 3 and bonded to the inner surfaces of these sheets 2, 3 along the end portions 2a, 3a. The fixed side edge portions 12c of the leak-proof sheets 12 are bonded to the outer surface of the topsheet 2.

In the side flaps 9, transversely opposite side edge portions 2b of the topsheet 2 extend outward beyond transversely opposite side edges 4b of the core 4 in the transverse direction. Transversely opposite side edge portions 3b of the backsheet 3 and the lateral portions 12d of the leak-proof sheets 12 extend further outward beyond the transversely opposite side edge portions 2b of the topsheet 2. In the side flaps 9, the side edge portions 2b of the topsheet 2 are interposed between the side edge portions 3b of the backsheet 3 and the fixed side edge portions 12a of the leak-proof sheets 12. The backsheet 3 and the leak-proof sheet 12 are overlaid along the transversely opposite side edge portions 3b and lateral portions 12d, which are extending outward beyond the transversely opposite side edge portions 2b of the topsheet 2, and the respective inner surfaces of these sheets 3, 12 are bonded together along the side edge portions 3b and the lateral portions 12d. The thigh-surrounding elastic members 11 are interposed between the side edge portions 3b of the backsheet 3 and the lateral portions 12d of the leak-proof sheets 12 and bonded to the inner surfaces of these sheets 3, 12 along the side edge portions 3b and the lateral portions 12d.

Each of the tape fasteners 13 has a fixed end portion 16 secured to the associated side flap 9 and a free end portion 17 extending outward from the fixed end portion 16 in the transverse direction. The fixed end portion 16 has a substantially rectangular shape which is relatively long in the longitudinal direction, first and second outer corners 18, 19 put aside toward a side edge 9a of the associated side flap 9, and first and second inner corners 20, 21 put aside toward the middle of the diaper 1A. The fixed end portion 16 is interposed between the side edge portion 3b of the backsheet 3 and the lateral portion 12d of the leak-proof sheet 12 and bonded to the inner surfaces of these sheets 3, 12 along the side edge portion 3b and the lateral portion 12d.

In each of the tape fasteners 13, the free end portion 17 is coated on its surface facing a wearer's body with a self-adhesive 22 (anchoring means), leaving a distal region 23 to be held by fingers. In the rear waist region 7, release paper 24 coated with a release agent (not shown) is bonded to the outer surface of the leak-proof sheet 12 along its lateral portion 12d. So long as the diaper 1A is not in use, the free end portion 17 of the tape fastener 13 is folded inward in the transverse direction of the diaper 1A and temporarily fixed to the release paper 24 in such a manner to be released by means of the self-adhesive 22. Of the inner and outer corners 18, 19, 20, 21 of the tape fastener 13, the first and second outer corners 18, 19 have respective surfaces facing the wearer's body covered with the first zone S1 of the associated side flap 9.

The first zone S1 is formed by the lateral portion 12d of the leak-proof sheet 12. More specifically, the first zone S1 is defined in the rear waist region 7 by the lateral portion 12d of the leak-proof sheet 12 folded inward along the side edge 9a of the associated side flap 9 in the transverse direction of the diaper 1A and bonded in a doubled over state. Consequently, the first zone of the leak-proof sheet 12 has a basis weight higher than that of the remaining zone, i.e., a second zone S2.

To wear the diaper 1A, the free end portions 17 of the respective tape fasteners 13 are peeled off from the releasing paper 24 and unfolded outward in the transverse direction of the diaper 1A, then the side flaps 9 in the rear waist region 7 are placed upon the outer sides of the side flaps 9 in the front waist region 5, the free end portions 17 of the respective tape fasteners 13 are anchored to the outer surface of the target tape strip 14 by means of the self-adhesive 22 so as to connect the front and rear waist regions 5, 7 to each other. With the diaper 1A having the front and rear waist regions 5, 7 connected to each other in this manner, a waist-hole and a pair of leg-holes lying below the waist-hole are defined though not shown.

In the case of the diaper disclosed by the above-cited Publication, the first and second outer corners of the respective fixed end portions lying adjacent the free end portions are apt to move vertically as well as laterally as movement of the wearer causes the free end portions of the respective tape fasteners to move vertically as well as laterally. With a consequence, the side flaps in the front waist region may be curled up and the side flaps in the rear waist region may contact the wearer's body. If the first and second outer corners further move vertically, these outer corners exposed on the outer surface of the topsheet would sometimes bite into the wearer's body and give the wearer pain and/or uncomfortable feeling.

In the case of the diaper 1A according to this invention, on the contrary, there is no anxiety that these outer corners 18, 19 might be exposed externally of the lateral portions 12d of the respective leak-proof sheets 12 in the first zones S1 and/or any level difference might be defined between peripheral edges of these outer corners 18, 19 and the lateral portions 12d of the respective leak-proof sheets 12 even when the side flaps 9 in the rear waist region 7 come in contact with the wearer's body. This is for the reason that the first and second outer corners 18, 19 of the fixed end portions 16 of the respective tape fasteners 13 are covered with the first zones S1 defined by the respective doubled-over lateral portions 12d of the leak-proof sheets 12 and these first zones S1 have basis weight higher than that of the second zones S2 of the leak-proof sheets 12. In this way, it is not apprehended that these outer corners 18, 19 might give the wearer pain and/or uncomfortable feeling.

In the diaper 1A, the first zone S1 has a basis weight in a range of 15-100 g/m$^2$, preferably in a range of 25-60 g/m$^2$. The second zone S2 has a basis weight in a range of 10-30 g/m$^2$, preferably in a range of 15-25 g/m$^2$. The tape fastener 13 has a flexural stiffness in a range of 0.3-10 g cm$^2$/cm as measured using KES-FB-2 of KATO TECH Corporation.

If the basis weight of the first zone S1 is less than 15 g/m$^2$, the first and second outer corners 18, 19 of the fixed end portion 16 in each of the tape fasteners 13 would be apt to be exposed externally of the lateral portion 12d of the associated leak-proof sheet 12 and these outer corners 18, 19 would sometimes give the wearer pain and/or uncomfortable feeling. On the other hand, the basis weight of the first zone S1 exceeding 100 g/m$^2$ would unacceptably increase its stiffness as well as its bulkiness and, in consequence, the first zone S1 would sometimes give the wearer pain and/or uncomfortable feeling. The basis weight of the second zone S2 less than 10 g/m$^2$ would result in breakage of the lateral portion 12d of the leak-proof sheet 12 and/or deteriorate the water-resistance in the side flap 9. On the other hand, the basis weight of the second zone S2 exceeding 30 g/m$^2$ would deteriorate the breathability in the side flap 9, depending on the basis weight of the backsheet 3.

If the flexural stiffness of the tape fastener 13 is less than 0.3 g·cm$^2$/cm, the free end portion 16 of the tape fastener 13 would be readily movable vertically as well as laterally even after the diaper 1A has been worn and reliable connection between the front and rear waist regions 5, 7 would not be ensured. If the flexural stiffness of the tape fastener 13 exceeds 10 g·cm$^2$/cm, the first and second outer corners 18, 19 of the fixed end portion 16 would be apt to be exposed externally of the lateral portion 12d of the leak-proof sheet 12 even when these outer corners 18, 19 are covered with the first zone S1 defined by the lateral portion 12d of the leak-proof sheet 12.

In the diaper 1A, the topsheet 2 is longitudinally curved inside and contraction of the elastic members 15 causes the free side edge portions 12b of the respective leak-proof sheets 12 to rise on the topsheet 2. The free side edge portions 12b of the respective leak-proof sheets 12 thereby form barriers against bodily discharges and prevent bodily discharges from leaking beyond the side flaps 9.

Figure 3:
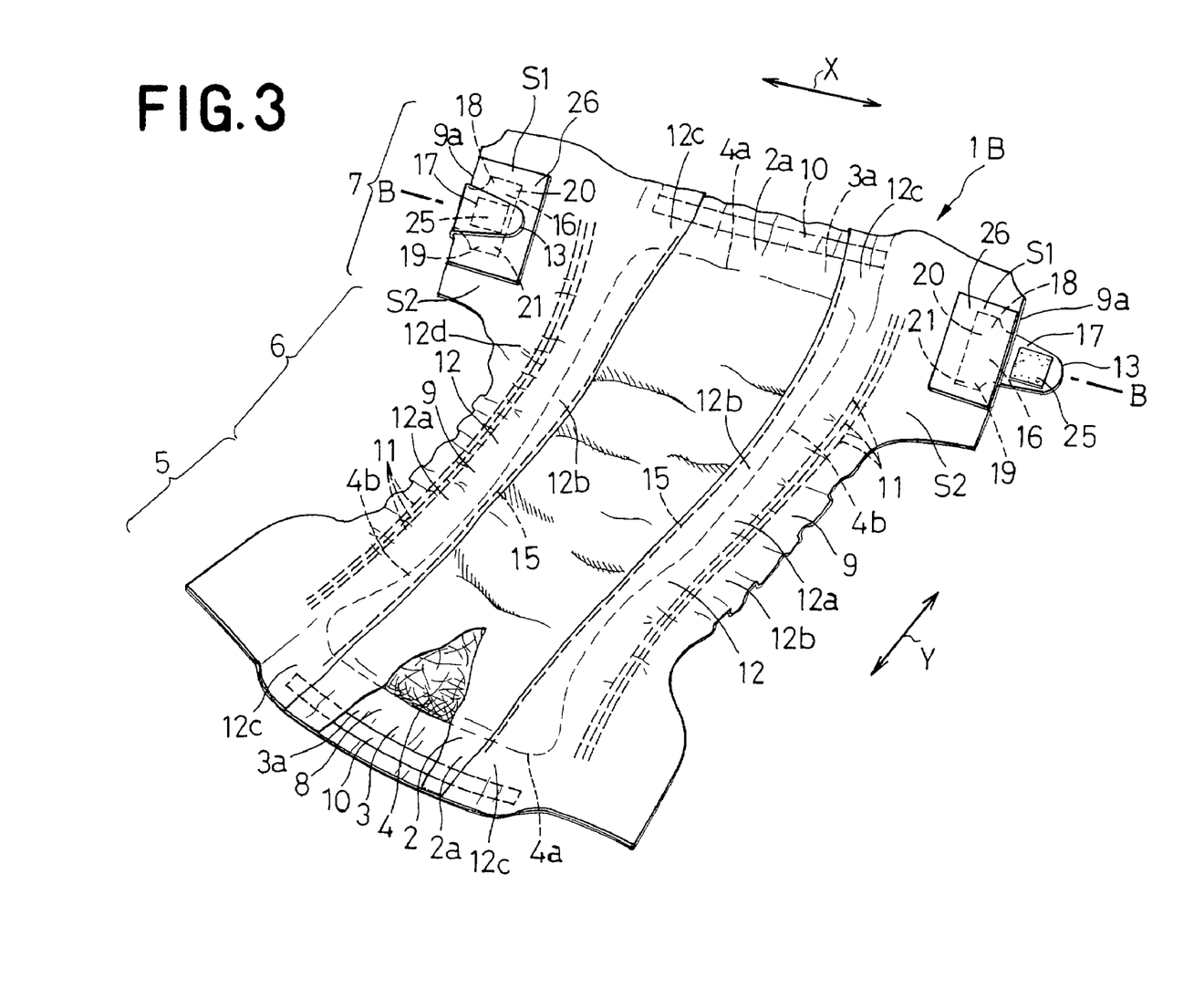
FIG. 3 is a partially cutaway perspective view of the disposable diaper according to one preferred embodiment of this invention.
Figure 4:
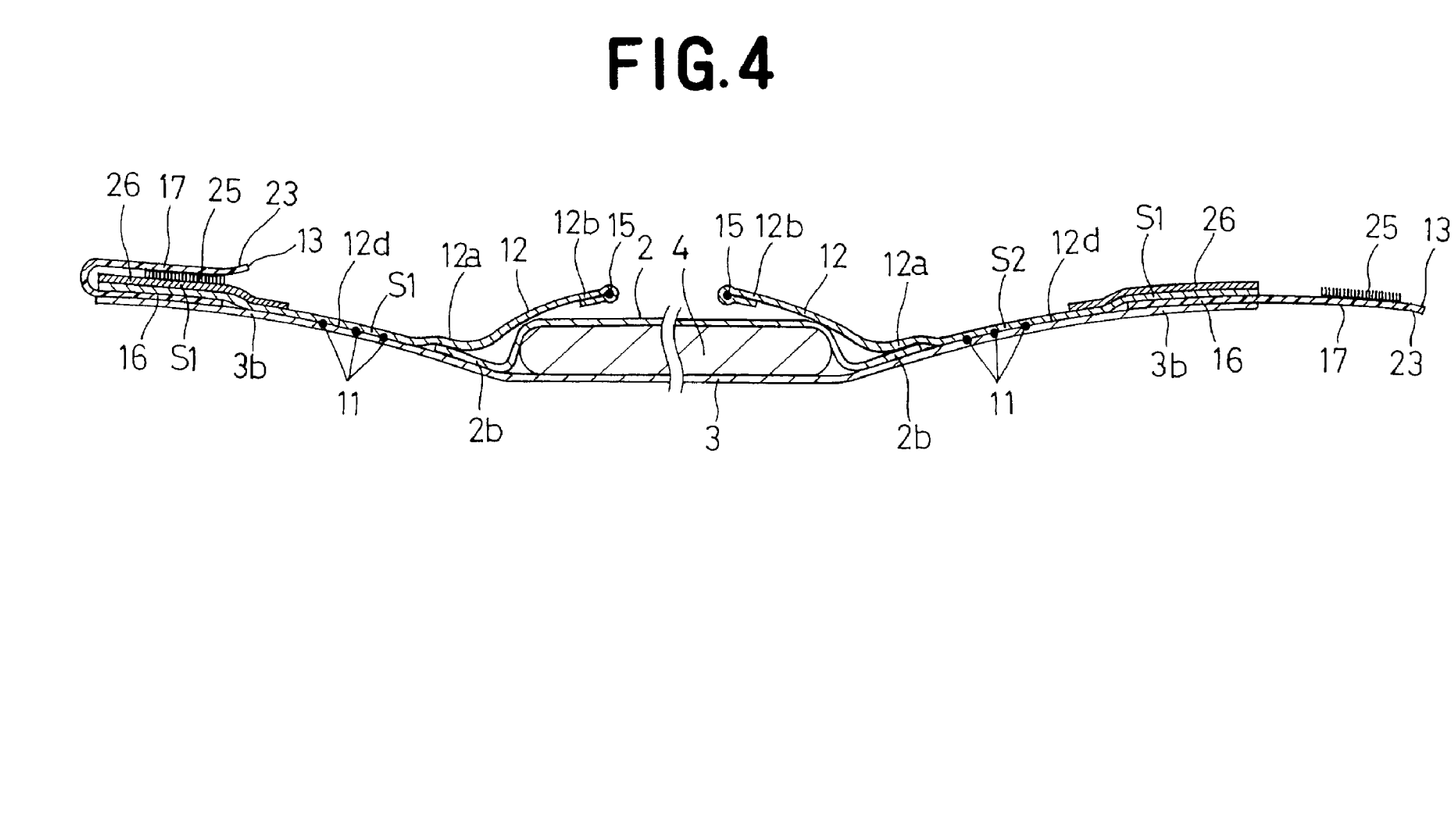
FIG. 4 is sectional view taken along a line B-B in FIG. 3.

FIG. 3 is a partially cutaway perspective view of the disposable diaper 1B according to one preferred embodiment of this invention and FIG. 4 is a sectional view taken along a line B-B in FIG. 3. In FIG. 3 shows one of tape fasteners 13 as its free end portion 17 has been unfolded outward in a transverse direction of the diaper 1B. In FIG. 3, the transverse direction is indicated by an arrow X and the longitudinal direction is indicated by an arrow Y. The diaper 1B of FIG. 3 is distinguished from the diaper 1A of FIG. 1 in its arrangement as will be described.

In this diaper 1B, the backsheet 3 is made of a hydrophobic fibrous nonwoven fabric and no target tape strip is attached to the outer surface of the backsheet 3 in the front waist region 5. In the case of this diaper 1B, the free end portions 17 of the respective tape fasteners 13 are provided on respective surfaces facing the wearer's body with a hook members 25 (anchoring means) each cooperating with a loop member to constitute so-called a mechanical fastener. The fixed end portion 16 of the tape fastener 13 has its surface facing the wearer's body entirely covered with the first zone S1 of the associated side flap 9.

The first zone S1 is formed by the lateral portion 12d of the leak-proof sheet 12 and the fibrous nonwoven fabric 26 (sheet). In the first zone S1, the fibrous nonwoven fabric 26 is placed upon and bonded to the outer surface of the lateral portion 12d. With a consequence, the first zone S1 has a basis weight higher than that of the second zone S2 defined by the leak-proof sheet 12 except for the first zone S1. So far as the basis weight of the first and second zones S1, S2 and the flexural stiffness of the tape fasteners 13 are concerned, the diaper 1B is the same as the diaper 1A of FIG. 1.

In the diaper 1B, free end portions 17 of the tape fasteners 13 are folded back inward in a transverse direction of the diaper 1B and temporarily fixed to the fibrous nonwoven fabric 26 by means of the hook members 25. In the case of this diaper 1B, the front and rear waist regions 5, 7 can be connected to each other by pressing the free end portions 17 of the tape fasteners 13 against the outer surface of the backsheet 3 in the front waist region 5 so as to bring the hook members 25 in engagement with component fibers of the nonwoven fabric.

In the case of the diaper 1B, there is no anxiety that the first and second outer corners 18, 19 as well as the first and second inner corners 20, 21 of the fixed end portion 16 might be exposed externally of the fibrous nonwoven fabric 26 in the first zone S1 and these inner and outer corners 18, 19, 20, 21 might give the wearer pain and/or uncomfortable feeling even if the side flaps 9 in the rear waist region 7 come in contact with the wearer's body and the fixed end portions 16 of the respective tape fasteners 13 move vertically as well as laterally during actual use of the diaper 1B. This is for the reason that the fixed end portions 16 of the respective tape fasteners 13 are entirely covered with the respective first zones S1 defined by the lateral portions 12d of the respective leak-proof sheets 12 and the fibrous nonwoven fabric 26.

Figure 2A:
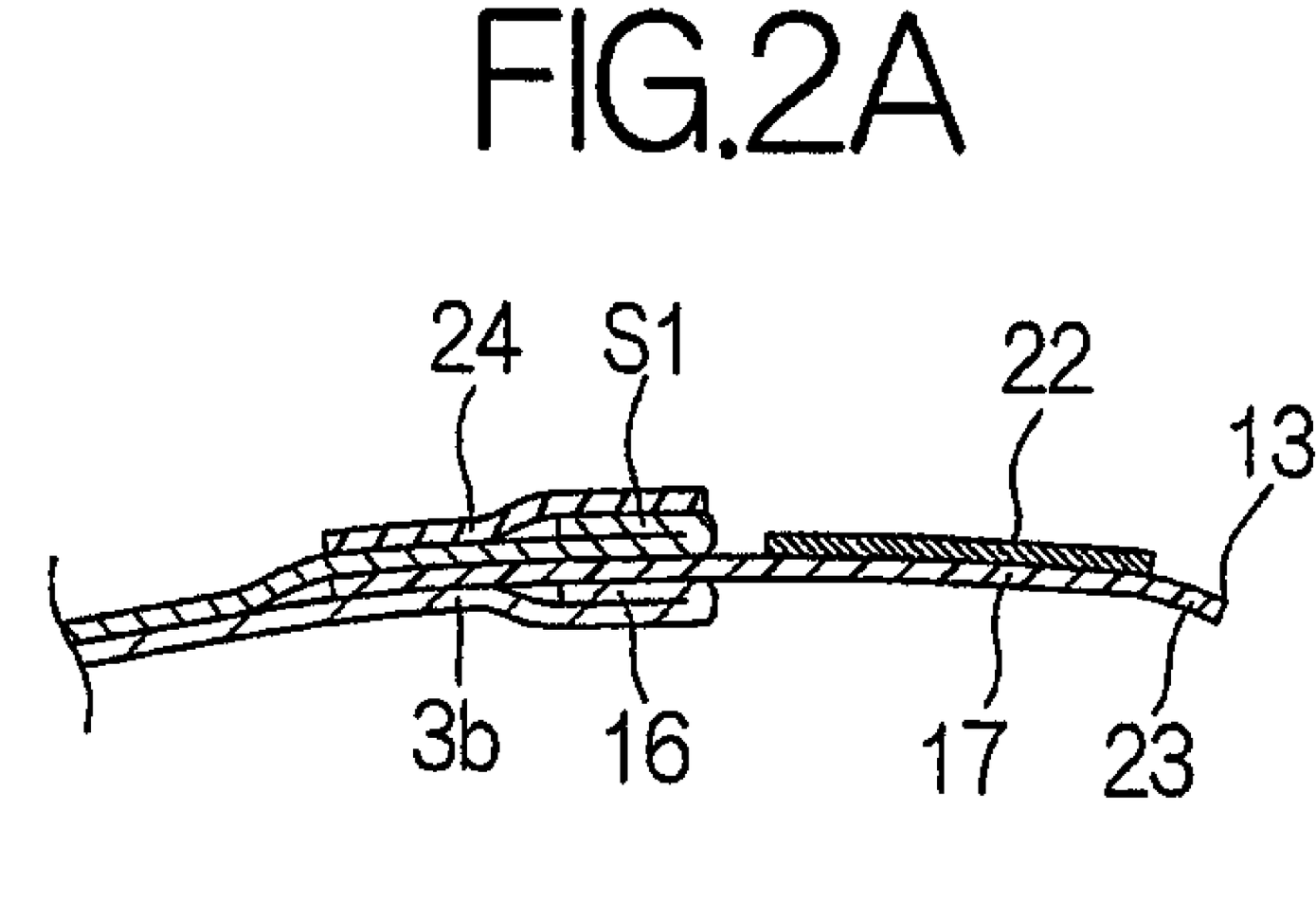
FIG. 2A is a fractional view similar to FIG. 2 and showing a different configuration of the side flap.

In the first zone S1 of the diaper 1A shown in FIG. 1, it is possible without departing from the scope of this invention to bond the lateral portion 12d of the leak-proof sheet 12 being folded more than three fold. In the diaper 1A of FIG. 1, it is possible without departing from the scope of this invention to form the first zone S1 by the lateral portion 12d of the leak-proof sheet 12 in the rear waist region 7 and the associated side edge portion 3b of the backsheet 3. In this case, the side edge portion 3b of the backsheet 3 is folded inward (FIG. 2A) along the side edge 9a of the associated side flap 9 in the transverse direction of the diaper 1A and bonded to the outer surface of the lateral portion 12d of the associated leak-proof sheet 12. In the first zone S1 of the diaper 1B shown in FIG. 3, it is also possible to place two or more layers of the fibrous nonwoven fabric 26 upon the lateral portion 12d of the respective leak-proof sheet 12 and to bond the lateral portion 12d and these layers of the fibrous nonwoven fabric 26 together.

While the first zone S1 is illustrated to be formed by folding the lateral portion 12d of the leak-proof sheet 12 in the diaper 1A or to be formed by placing and bonding the fibrous nonwoven fabric 26 upon and to the lateral portion 12d of the leak-proof sheet 12 in the diaper, there may be further another arrangement in which the leak-proof sheet 12 is formed by a single layer of fibrous nonwoven fabric and an amount of the component fiber constituting the leak-proof sheet 12 in the first zone S1 is larger than that of the leak-proof sheet 12 in the second zone S2 except for the first zone S1 so that the basis weight of the first zone S1 is higher than that of the second zone S2. In the diapers 1A, 1B, it is also possible without departing from the scope of this invention to provide the respective side flaps 9 in the rear waist region 7 with two or more tape fasteners 13 arranged in the longitudinal direction.

A stock material for the topsheet 2 may be selected from a group of materials consisting of a hydrophilic fibrous nonwoven fabric, hydrophobic fibrous nonwoven fabric having a plurality of fine pores and plastic film having a plurality of fine pores. A stock material for the backsheet 3 of the diaper 1A shown in FIG. 1 may be selected from a group of materials consisting of a hydrophobic fibrous nonwoven fabric, a breathable but liquid-impervious plastic film, a composite nonwoven fabric comprising two or more hydrophobic fibrous nonwoven fabric layers laminated one with another and a composite sheet comprising a hydrophobic fibrous nonwoven fabric and a breathable but liquid-impervious plastic film laminated with each other. For the leak-proof sheets 12, a hydrophobic fibrous nonwoven fabric or a breathable but liquid-impervious plastic film may be selectively used.

It is also possible to use, as a stock material for the backsheet 3 and the leak-proof sheets 12 of the diaper 1A, 1B illustrated as the embodiments of this invention, a composite nonwoven fabric comprising a melt blown fibrous nonwoven fabric having high water-resistance sandwiched between two layers of spun bond fibrous nonwoven fabric having high strength and flexibility.

Nonwoven fabric may be selected from a group of materials consisting products obtained by spun lacing, needle punching, melt blowing, thermal bonding, spun bonding, chemical bonding and air-through processes. Component fibers of the nonwoven fabric may be selected from a group of materials including polyolefine-, polyester- and polyamide-based fibers and core-sheath-type and side-by-side-type conjugated fibers of polyethylene/polypropylene and polyethylene/polyester.

The tape fastener 13 may be formed using a flexible plastic sheet or a flexible craft paper. Using such a stock material, the tape fasteners 13 of these diapers 1A, 1B shown as the embodiments of this invention are more stiff than the top- and backsheets 2, 3, the leak-proof sheets 12 and the fibrous nonwoven fabric 26, i.e., these sheets 2, 3, 12 and the fibrous nonwoven fabric 26 are more flexible than the tape fasteners 13. The target tape strip 15 may be formed using a flexible plastic film.

The core 4 is formed by a mixture of fluff pulp and superabsorbent polymer particles or a mixture of fluff pulp, superabsorbent polymer particles and thermoplastic synthetic resin fiber, in any case, compressed to a desired thickness. Preferably, the core 4 is entirely covered with a tissue paper in order to prevent the core 4 from getting out of shape or to prevent the polymer particles from falling off. The polymer particles may be selected from a group of materials consisting of a starch-based polymer, a cellulose-base polymer and a synthetic polymer.

Bonding of the top- and backsheets 2, 3, the leak-proof sheets 12, the fibrous nonwoven fabric 26, the core 4 and the elastic members 10, 11, 15 may be carried out using a hot melt adhesive or welding techniques such as heat-sealing or ultrasonic sealing.

This invention is applicable not only to the open-type disposable diaper 1A, 1B but also to the open-type diaper cover adapted to be used with the liquid-absorbent pad attached to the inner side of this diaper cover.

The open-type disposable wearing article according to this invention is primarily characterized in the arrangement such that the fixed end portions of the respective tape fasteners are covered with the first zones of the respective side flaps and these first zones have a basis weight higher than that of the second zones defined by the side flaps except for the first zones. Such an arrangement is effective to eliminate the problem that the fixed end portions of the tape fasteners might give the wearer pain and/or uncomfortable feeling even when the side flaps in the rear waist region are curled up and come in direct contact with the wearer's body.

In the embodiment of this invention in which the fixed end portions of the respective tape fasteners have the first and second outer corners and the first and second inner corners of which at least the first and second outer corners are covered with the first zones of the respective side flaps, there is no anxiety that the outer corners might be exposed externally of the first zones and might give the wearer pain and/or uncomfortable feeling even if the first and second outer corners of the respective fixed end portions move vertically as well as laterally as the free end portions of the respective tape fasteners move vertically as well as laterally.

What is claimed is:

1. An open-type disposable wearing article, comprising
side flaps extending in a longitudinal direction of the article and end flaps extending in a transverse direction of the article;
front and rear waist regions and a crotch region extending in said longitudinal direction between said waist regions;
flexible tape fasteners for attaching said front and rear waist regions to each other, each of said tape fasteners being attached to one of said side flaps in said rear waist region, and having a fixed end portion bonded to said respective side flap and a free end portion extending outward from said fixed end portion in the transverse direction, said free end portion having an anchoring element adapted to be anchored on said front waist region;
a liquid pervious topsheet, a liquid impervious backsheet and an absorbent core disposed between said topsheet and backsheet; and
a pair of liquid impervious sheets defining barrier flaps on transversely opposite sides of said absorbent core for preventing lateral leakage of bodily discharge;
wherein said liquid impervious sheets and said backsheet extend continuously in the transverse direction beyond transversely opposite side edges of said topsheet and said absorbent core to define said side flaps,
wherein each of said side flaps comprises
a first zone in which said fixed end portion of the respective tape fastener is sandwiched between the backsheet and a respective one of the liquid impervious sheets;

a second zone located transversely inward of said first zone; and a layer of a material different from those of said backsheet and said liquid impervious sheets, said layer being bonded to the first zone of said side flap whereby said first zone has a basis weight higher than that of said second zone, wherein, in each of said side flaps, one of said backsheet and the respective liquid impervious sheet is folded along a longitudinal edge of said side flap in at least said first zone, and comprises a lower fold and an upper fold placed on the lower fold; and said upper fold and said fixed end portion of the respective tape fastener do not overlap throughout an entire area of said fixed end portion.

2. A disposable wearing article, comprising side flaps extending in a longitudinal direction of the article and end flaps extending in a transverse direction of the article;

front and rear waist regions and a crotch region extending in said longitudinal direction between said waist regions;

flexible tape fasteners for attaching said front and rear waist regions to each other, each of said tape fasteners being attached to one of said side flaps in said rear waist region, and having a fixed end portion bonded to said respective side flap and a free end portion extending outward from said fixed end portion in the transverse direction, said free end portion having an anchoring element adapted to be anchored on said front waist region;

a liquid pervious topsheet, a liquid impervious backsheet and an absorbent core disposed between said topsheet and backsheet; and a pair of liquid impervious sheets defining barrier flaps on transversely opposite sides of said absorbent core for preventing lateral leakage of bodily discharge;

wherein said liquid impervious sheets and said backsheet extend continuously in the transverse direction beyond transversely opposite side edges of said topsheet and said absorbent core to define said side flaps, wherein each of said side flaps comprises a first zone in which said fixed end portion of the respective tape fastener is sandwiched between the backsheet and a respective one of the liquid impervious sheets; and a second zone located transversely inward of said first zone, and wherein, in each of said side flap, the liquid impervious sheet is folded along a longitudinal edge of said side flap in at least said first zone, whereby said first zone has a basis weight higher than that of said second zone.

3. A disposable wearing article, comprising side flaps extending in a longitudinal direction of the article and end flaps extending in a transverse direction of the article;

front and rear waist regions and a crotch region extending in said longitudinal direction between said waist regions;

flexible tape fasteners for attaching said front and rear waist regions to each other, each of said tape fasteners being attached to one of said side flaps in said rear waist region, and having a fixed end portion bonded to said respective side flap and a free end portion extending outward from said fixed end portion in the transverse direction, said free end portion having an anchoring element adapted to be anchored on said front waist region;

a liquid pervious topsheet, a liquid impervious backsheet and an absorbent core disposed between said topsheet and backsheet; and a pair of liquid impervious sheets defining barrier flaps on transversely opposite sides of said absorbent core for preventing lateral leakage of bodily discharge;

wherein said liquid impervious sheets and said backsheet extend continuously in the transverse direction beyond transversely opposite side edges of said topsheet and said absorbent core to define said side flaps, wherein each of said side flaps comprises a first zone in which said fixed end portion of the respective tape fastener is sandwiched between the backsheet and a respective one of the liquid impervious sheets; and a second zone located transversely inward of said first zone, and wherein, in each of said side flap, the backsheet is folded along a longitudinal edge of said side flap in at least said first zone, whereby said first zone has a basis weight higher than that of said second zone.

4. An open-type disposable wearing article, comprising side flaps extending in a longitudinal direction of the article and end flaps extending in a transverse direction of the article;

front and rear waist regions and a crotch region extending in said longitudinal direction between said waist regions;

flexible tape fasteners for attaching said front and rear waist regions to each other, each of said tape fasteners being attached to one of said side flaps in said rear waist region, and having a fixed end portion bonded to said respective side flap and a free end portion extending outward from said fixed end portion in the transverse direction, said free end portion having an anchoring element adapted to be anchored on said front waist region;

a liquid pervious topsheet, a liquid impervious backsheet and an absorbent core disposed between said topsheet and backsheet; and a pair of liquid impervious sheets defining barrier flaps on transversely opposite sides of said absorbent core for preventing lateral leakage of bodily discharge;

wherein said liquid impervious sheets and said backsheet extend continuously in the transverse direction beyond transversely opposite side edges of said topsheet and said absorbent core to define said side flaps, wherein each of said side flaps comprises a first zone in which said fixed end portion of the respective tape fastener is sandwiched between the backsheet and a respective one of the liquid impervious sheets;

a second zone located transversely inward of said first zone; and a layer of a material different from those of said backsheet and said liquid impervious sheets, said layer being bonded to the first zone of said side flap whereby said first zone has a basis weight higher than that of said second zone, wherein the liquid impervious sheets extend continuously inwardly in the transverse direction beyond transversely opposite side edges of said core and terminate at inner edges; and said inner edges of said liquid impervious sheets have elastic members bonded thereto to bias the inner edges of said liquid impervious sheets to rise above the topsheet to define said barrier flaps.

5. The wearing article according to claim 4,
wherein each of the transversely opposite side edges of said topsheet is sandwiched between said backsheet and one of said liquid impervious sheets.

6. An open-type disposable wearing article, comprising
side flaps extending in a longitudinal direction of the article and end flaps extending in a transverse direction of the article;
front and rear waist regions and a crotch region extending in said longitudinal direction between said waist regions;
flexible tape fasteners for attaching said front and rear waist regions to each other, each of said tape fasteners being attached to one of said side flaps in said rear waist region, and having a fixed end portion bonded to said respective side flap and a free end portion extending outward from said fixed end portion in the transverse direction, said free end portion having an anchoring element adapted to be anchored on said front waist region;
a liquid pervious topsheet, a liquid impervious backsheet and an absorbent core disposed between said topsheet and backsheet; and
a pair of liquid impervious sheets defining barrier flaps on transversely opposite sides of said absorbent core for preventing lateral leakage of bodily discharge;
wherein said liquid impervious sheets and said backsheet extend continuously in the transverse direction beyond transversely opposite side edges of said topsheet and said absorbent core to define said side flaps,
wherein each of said side flaps comprises
a first zone in which said fixed end portion of the respective tape fastener is sandwiched between the backsheet and a respective one of the liquid impervious sheets;
a second zone located transversely inward of said first zone; and
a layer of a material different from those of said backsheet and said liquid impervious sheets, said layer being bonded to the first zone of said side flap whereby said first zone has a basis weight higher than that of said second zone,
wherein, in each of said side flaps,
one of said backsheet and the respective liquid impervious sheet is folded along a longitudinal edge of said side flap to define first and second folds one placed on top of the other; and
said first fold and said fixed end portion of the respective tape fastener do not overlap each other throughout an entire area of said fixed end portion.

7. The wearing article according to claim 6, wherein, in each of said side flaps,
the first zone is defined by said first fold, and
the second zone is defined by a remaining region of said side flap located transversely inward of said first zone and free of said first fold.

8. The wearing article according to claim 7, wherein, in each of said side flaps, said layer extends from the longitudinal side edge, across an entire width of said first zone and further into the second zone.

9. The wearing article according to claim 8, wherein, for each of said side flaps,
the fixed end portion of the respective tape fastener has four corners, the outer two of which are located in the first zone and covered by the first fold, whereas the other, inner two corners are located in the second zone, and
none of the corners are covered by the layer.

10. The wearing article according to claim 9, wherein each of said side flaps comprises two or more said layers bonded one on top another.

* * * * *